United States Patent [19]
Forestier et al.

[11] Patent Number: 6,071,502
[45] Date of Patent: Jun. 6, 2000

[54] PHOTOSTABLE SUNSCREEN COMPOSITIONS COMPRISING DIBENZOYLMETHANE COMPOUNDS AND 2-HYDROXYBENZOPHENONE-SUBSTITUTED SILANES/ ORGANOSILOXANES

[75] Inventors: Serge Forestier, Claye Souilly; Hervé Richard, Villepinte, both of France

[73] Assignee: Societe L'Oreal S.A., Paris, France

[21] Appl. No.: 09/377,739

[22] Filed: Aug. 20, 1999

[30] Foreign Application Priority Data

Aug. 21, 1998 [FR] France ................... 98 10632

[51] Int. Cl.[7] .............. A61K 7/42; A61K 7/44; A61K 7/00
[52] U.S. Cl. .............. 424/59; 424/60; 424/400; 424/401
[58] Field of Search ................ 424/59, 60, 400, 424/401

[56] References Cited

FOREIGN PATENT DOCUMENTS 0675108  10/1995  European Pat. Off. .
93/10745  6/1993  WIPO .

OTHER PUBLICATIONS

Chemical Abstracts, vol. 114, No. 20, May 20, 1991, Abstract No. 186892.
Chemical Abstracts, vol. 110, No. 24, Jun. 12, 1989, Abstract No. 213551.
Chemical Abstracts, vol. 116, No. 21, May 25, 1992, Abstract No. 214698.
Chemical Abstracts, vol. 119, No. 24, Dec. 13, 1993, Abstract No. 251293.
Chemical Abstracts, vol. 118, No. 8, Feb. 22, 1993, Abstract No. 66597.
Chemical Abstracts, vol. 116, No. 19, May 11, 1992, Abstract No. 194587.

*Primary Examiner*—Shelley A. Dodson
*Attorney, Agent, or Firm*—Burns, Doane, Swecker & Mathis, L.L.P.

[57] ABSTRACT

Improvedly photostable, topically applicable cosmetic/dermatological sunscreen compositions well suited for the photoprotection of human skin and/or hair against the damaging effects of UV-irradiation, particularly solar radiation, comprise (1) a UV-photoprotecting effective amount of at least one dibenzoylmethane sunscreen compound and (2) a photostabilizing effective amount of at least one silane or organosiloxane bearing a 2-hydroxybenzophenone substituent.

43 Claims, No Drawings

PHOTOSTABLE SUNSCREEN COMPOSITIONS COMPRISING DIBENZOYLMETHANE COMPOUNDS AND 2-HYDROXYBENZOPHENONE-SUBSTITUTED SILANES/ORGANOSILOXANES

CROSS-REFERENCE TO PRIORITY APPLICATION

This application claims priority under 35 U.S.C. §119 of FR-98/10632, filed Aug. 21, 1998, hereby expressly incorporated by reference and relied upon.

BACKGROUND OF THE INVENTION

1. Technical Field of the Invention

The present invention relates to novel improvedly photostable sunscreen compositions comprising at least one UV-photoprotecting compound and a photostabilizing effective amount of at least one silane or organosiloxane compound bearing a 2-hydroxybenzophenone substituent.

2. Description of the Prior Art

It is known to this art that light radiation with wavelengths of from 280 nm to 400 nm promotes tanning of the human epidermis, and that light rays with wavelengths more particularly from 280 to 320 nm, i.e., UV-B irradiation, cause skin burns and erythema which may be harmful to the natural development of the tan. For these reasons, as well as for aesthetic reasons, there is constant demand for means of controlling this natural tanning in order thereby to control the color of the skin; this UV-B radiation should thus be screened from the skin.

It is also known to this art that UV-A radiation, with wavelengths of from 320 to 400 nm, which causes tanning of the skin, also adversely affects it, especially in the case of sensitive skin or of skin which is continually exposed to solar radiation. UV-A rays cause, in particular, a loss of elasticity of the skin and the appearance of wrinkles, leading to premature skin aging. Such irradiation promotes triggering of the erythemal reaction or amplifys this reaction in certain individuals and may even be the source of phototoxic or photoallergic reactions. Thus, for aesthetic and cosmetic reasons, such as conservation of the natural elasticity of the skin, for example, an ever-increasing number of individuals wish to control the effect of UV-A rays on their skin. It is thus desirable to also screen out UV-A radiation.

In this respect, a particularly advantageous class of UV-A screening agents currently includes dibenzoylmethane derivatives, and in particular 4-tert-butyl-4'-methoxydibenzoylmethane, which effectively have a high intrinsic power of absorption. These dibenzoylmethane derivatives, which are compounds well known per se as screening agents that are active in the UV-A range, are particularly described in FR-A-2,326,405 and FR-A-2,440,933, as well as in EP-A-0,114,607; 4-(tert-butyl)-4'-methoxydibenzoylmethane is moreover currently commercially available under the trademark "Parsol 1789" from Givaudan.

Unfortunately, it too is known that dibenzoylmethane compounds are relatively sensitive to ultraviolet radiation (especially UV-A), i.e., more precisely, they are known to have an annoying tendency to become degraded more or less quickly under the action or influence of this radiation. Thus, this substantial lack of photochemical stability of dibenzoylmethane derivatives with respect to ultraviolet radiation, to which they are by nature intended to be subjected, does not guarantee constant protection during prolonged exposure to the sun, such that, in a restrictive manner, repeated applications at regular, close intervals of time must be carried out by the user in order to obtain effective protection of the skin against UV rays.

Too, EP-A-0,709,080 proposes combining benzalmalonate derivatives with the dibenzoylmethane derivatives in order to reduce the photoinstability of said dibenzoylmethane compounds. However, the photostabilization of the dibenzoylmethane derivatives with respect to UV radiation to date remains a vexing problem which still not been solved entirely satisfactorily.

It has also been proposed, in EP-A-0,843,996, to formulate 2-hydroxybenzophenone hydrocarbon-based derivatives such as 2-hydroxy-4-methoxybenzophenone or 2-hydroxy-4-methoxybenzophenone-5-sulfonic acid with the dibenzoylmethane compounds in order to reduce the photoinstability of said dibenzoylmethane compounds.

Another difficulty, independent of that mentioned above, encountered with dibenzoylmethane compounds is that these are lipophilic UV-screening agents which also present the drawback of being solid at room temperature. Consequently, including same in sunscreen cosmetic compositions entails certain constraints as regards their formulation and practical applications thereof in particular in respect of determining solvents for properly dissolving same, whether alone or together with other screening agents. In this regard, oils such as esters are conventionally employed, more particularly $C_{12}$–$C_{15}$ alkyl benzoates ("Finsolv TN" marketed by Finetex), or triglycerides and especially $C_8$–$C_{12}$ fatty acid triglycerides ("Miglyol 812" marketed by Hüls), but these various materials exhibit solubilizing properties vis-a-vis the abovementioned screening agents which still remain insufficient.

The sunscreen/antisun formulations based on dibenzoylmethane compounds and 2-hydroxy-4-methoxybenzophenone or 2-hydroxy-4-methoxybenzophenone-5-sulfonic acid, as described in EP-A-0,843,996, do not satisfactorily solve this problem of solubility of said dibenzoylmethane derivatives.

SUMMARY OF THE INVENTION

It has now surprisingly and unexpectedly been determined that formulating an effective amount of a silane or organosiloxane compound bearing a 2-hydroxybenzophenone substituent with the dibenzoylmethane compounds mentioned above, the photochemical stability (or photostability) of such dibenzoylmethane compounds is substantially and markedly enhanced.

It has now also been determied that certain silane or organosiloxane compounds substituted by a 2-hydroxybenzophenone function, constituting the photostabilizing agents according to this invention, equally very surprising compared with the known hydrocarbon-based organic screening agents derived from 2-hydroxybenzophenone, are particularly effective solvents for screening agents of the type derived from dibenzoylmethane, such as, for example, 4-(tert-butyl)-4'-methoxydibenzoylmethane; this permits, for an equal amount of solvent, using larger amounts of UV screening agents.

Briefly, then, the present invention features enhancing the stability of at least one dibenzoylmethane compound with respect to UV radiation, by intimately admixing therewith an effective photostabilizing amount of a silane or organosiloxane bearing a 2-hydroxybenzophenone substituent.

DETAILED DESCRIPTION OF BEST MODE AND SPECIFIC/PREFERRED EMBODIMENTS OF THE INVENTION

More particularly according to the present invention, the cosmetic and/or dermatological compositions formulated consistent herewith present the advantage of being particularly photostable, even after prolonged exposure to UV-A and UV-B irradiation. Such radiation can be of natural origin (sunlight) or artificial origin (UV lamp).

The present invention thus features formulating a silane or organosiloxane compound substituted by a 2-hydroxybenzophenone function into cosmetic or dermatological compositions containing at least one dibenzoylmethane sunscreen compound, to enhance the stability of said dibenzoylmethane sunscreen compounds with respect to UV irradiation.

As indicated above, the dibenzoylmethane compounds photostabilized according to the present invention are active species already well known per se and described, in particular, in FR-A-2,326,405, FR-A-2,440,933 and EP-A-0,114,607 mentioned above.

Per the present invention, one or more dibenzoylmethane derivatives can of course be formulated into the subject compositions.

Exemplary dibenzoylmethane compounds according to the present invention include:

2-Methyldibenzoylmethane;
4-Methyldibenzoylmethane;
4-Isopropyldibenzoylmethane;
4-Tert-butyldibenzoylmethane;
2,4-Dimethyldibenzoylmethane;
2,5-Dimethyldibenzoylmethane;
4,4'-Diisopropyldibenzoylmethane;
4,4'-Dimethoxydibenzoylmethane;
4-Tert-butyl-4'-methoxydibenzoylmethane;
2-Methyl-5-isopropyl-4'-methoxydibenzoylmethane;
2-Methyl-5-tert-butyl-4'-methoxydibenzoylmethane;
2,4-Dimethyl-4'-methoxydibenzoylmethane;
2,6-Dimethyl-4-tert-butyl-4'-methoxydibenzoylmethane.

Among the dibenzoylmethane indicated above, the most particularly preferred according to the present is 4-(tert-butyl)-4'-methoxydibenzoylmethane, especially that marketed under the trademark "Parsol 1789" by Givaudan. This screening agent has the following structural formula:

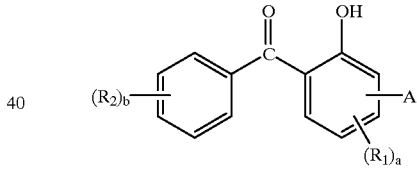

Another preferred dibenzoylmethane compound according to the present invention is 4-isopropyldibenzoylmethane, this screening agent being marketed under the trademark "Eusolex 8020" by Merck, and having the following structural formula:

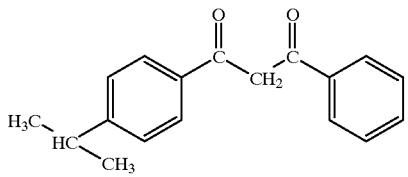

The dibenzoylmethane compound(s) comprising the compositions stabilized according to this invention advantageously constitute from 0.01% to 10% by weight, and preferably from 0.3% to 5% by weight, of the total weight of the composition.

The other constituent of the compositions according to the invention is a silane or organosiloxane compound substituted by a 2-hydroxybenzophenone function. These compounds are well known to the art and are described, as are various processes for the synthesis thereof, for example, FR-1,518,231; FR-2,200,275; U.S. Pat. Nos. 4,436,851; 4,321,400; 4,278,804, 4,328,346; 4,395,461; 4,467,082; EP-A-0,088,842; DD-208,470; U.S. Pat. Nos. 4,419,405; 4,477,499; 4,414,349; 4,555,545; 4,555,559; 4,696,969; DD-249,030; U.S. Pat. No. 4,868,251; JP-01096259; JP-02187437; EP-A-0,389,337; EP-A-0,475,149; U.S. Pat. No. 5,250,615; FR-2,657,351; JP-03287589; JP-03287588; EP-A-0,478,284; JP-04217622; EP-A-0,526,399; U.S. Pat. No. 5,310,845; EP-A-0,655,453; EP-A-0,667,379; EP-A-0,668,313; JP-08169815; U.S. Pat. No. 3,352,986 (each of these being expressly incorporated by reference herein).

Preferably, the silane or organosiloxane compound bearing a 2-hydroxybenzophenone substituent according to the present invention has the following formula (I):

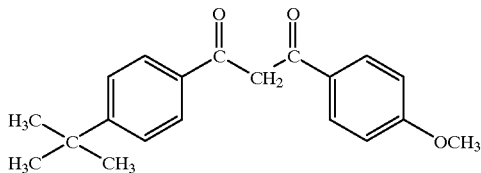

in which $R_1$ and $R_2$, which may be identical or different, are each a hydrogen atom, an OH radical, a saturated or unsaturated, linear or branched $C_1$–$C_{10}$ alkyl radical or a linear or branched $C_1$–$C_{10}$ alkoxy radical; a is an integer ranging from 1 to 3; b is an integer ranging from 1 to 5; A is a radical of formula —L—W wherein L is a divalent radical of formula (IIa) or (IIb) below:

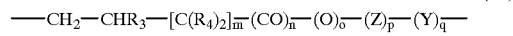

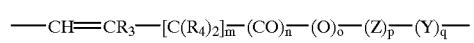

wherein $R_3$ and $R_4$, which may be identical or different, are each a hydrogen atom or a linear or branched $C_1$–$C_5$ alkyl radical; Z is a linear or branched, saturated or unsaturated $C_1$–$C_6$ diyl radical optionally substituted with a hydroxyl or linear or branched, saturated or unsaturated $C_2$–$C_8$ alkyl radical; Y represents —O—, —$NR_5$—, —$SO_2NH$—, —(CO)O—, —(CO)NH— or —O(CO)NH—, wherein $R_5$ represents hydrogen or a $C_1$–$C_5$ alkyl radical; m is an integer ranging from 0 to 10; n is 0 or 1; o is 0 or 1; p is 0 or 1; q is 0 or 1; W is a radical of one of the formulae (1), (2) or (3) below:

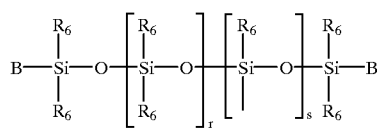
(1)

or

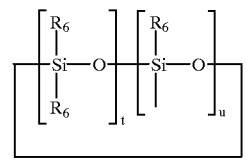
(2)

or

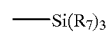
(3)

wherein the radicals $R_6$, which may be identical or different, are each a linear or branched $C_1$–$C_{30}$ alkyl, phenyl, 3,3,3-trifluoropropyl or trimethylsilyloxy radical, at least 80%, by number, of the radicals $R_6$ being methyl radicals; the radicals $R_7$, which may also be identical or different, are each a linear or branched $C_1$–$C_{30}$ alkyl or phenyl radical; the radicals B, which may be identical or different, are each radical $R_6$ or a radical X having the following formula:

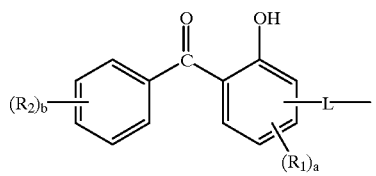

in which $R_1$, $R_2$, L, a and b are as defined above; r is an integer ranging from 0 to 200, inclusive; s is an integer ranging from 0 to 50, inclusive, with the proviso that, if s=0, at least one of the two radicals B is X; u is an integer ranging from 1 to 10, inclusive and t is an integer ranging from 0 to 10, inclusive, with the proviso that t+u is greater than or equal to 3.

Among the above compounds, particularly preferred are those satisfying at least one, preferably all, of the following conditions:

$R_1=R_2=R_3=R_4=H$;

n=0;

q=1.

Within this subgenus, the preferred compounds satisfy at least one, preferably all, of the following conditions:

$R_6$ is methyl;

B is methyl;

r ranges from 5 to 20, inclusive;

s ranges from 2 to 15, inclusive;

t+u ranges from 3 to 10, inclusive;

m=1;

$R_3$ is hydrogen or a methyl radical.

These compounds and process for preparing same are described, for example, in EP-A-0,389,377.

A second class of preferred compounds is that combining the compounds of formula (I) in which s=0.

These compounds, and process for preparing same, are described, in particular, in FR-A-2,657,351 and EP-A-0,655,453.

Exemplary compounds of formula (I) which are particularly preferred are those of the following formulae:

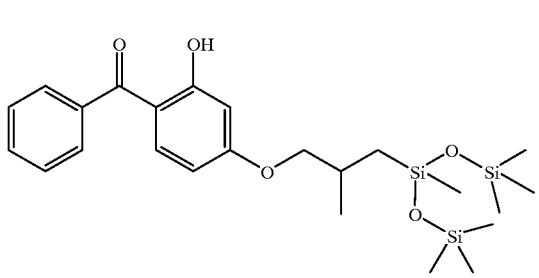
(4)

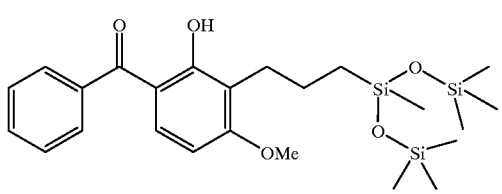
(5)

(6)
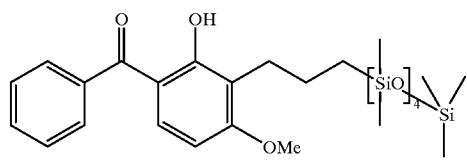
(7)
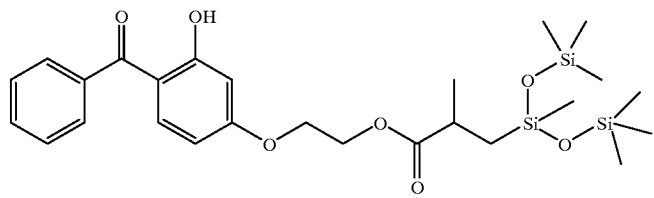
(8)
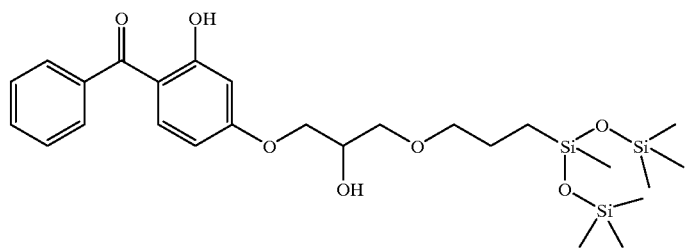
(9)
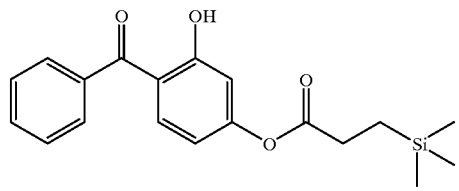
(10)
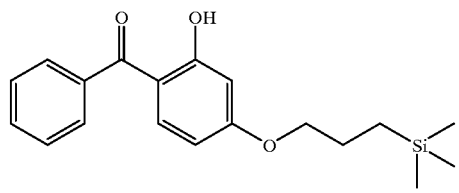
(11)
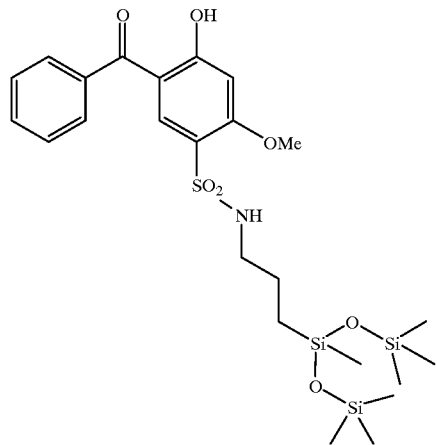

(12)

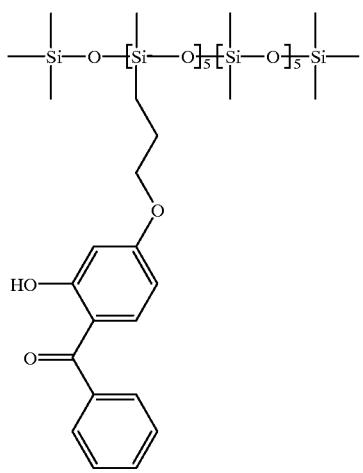

Among the compounds having the above formula (I) certain of these are themselves per se novel and constitute another aspect of the present invention.

This is the particular case for the compounds of above formula (I) in which p is 1; the radical Z is a linear or branched, saturated or unsaturated $C_1$–$C_6$ diyl radical containing a hydroxyl or linear or branched, saturated or unsaturated $C_2$–$C_8$ alkyl radical and $R_2$ is other than an OH group. Among these specific compounds, particularly exemplary is the above compound (8).

Another class of novel compounds of formula (I) includes the silane compounds in which W is a radical of formula (3); n is equal to 0 and $R_2$ is other than an OH group. Among these compounds, particularly exemplary is the above compound (10).

Consistent herewith, by the expression "effective amount of silane or organosiloxane compound bearing a 2-hydroxybenzophenone substituent" is intended an amount which is sufficient to provide an appreciable and significant improvement in the photostability of the dibenzoylmethane derivative(s) contained in the composition. The minimum amount of stabilizer to be formulated, which can vary depending on the nature of the cosmetically acceptable support (vehicle, diluent or carrier) selected for the composition, can be determined without any difficulty by means of a standard test for measuring photostability, as described in FR-A-2,607,700.

The silane or organosiloxane compounds substituted by a 2-hydroxybenzophenone function are advantageously present in the compositions according to the invention at a content at least equal to 0.5% by weight relative to the total weight of the composition. More preferably, this content ranges from 0.5% to 20% by weight relative to the total weight of the composition.

The cosmetic and/or dermatological compositions according to by the present invention can, of course, contain one or more additional hydrophilic or lipophilic UVA- and/or UVB-active sunscreens (absorbers). These additional screening agents are advantageously selected from among cinnamic derivatives, salicylic derivatives, benzylidene camphor derivatives, benzotriazole derivatives, benzimidazole derivatives, triazine derivatives, benzalmalonate derivatives, β,β'-diphenylacrylate derivatives, p-aminobenzoic acid derivatives, and the screening polymers and screening silicones described in WO-93/04665. Other examples of organic screening agents are provided in EP-A-0,487,404.

The compositions according to the invention can also contain agents for the artificial tanning and/or bronzing of the skin (self-tanning agents) such as, for example, dihydroxyacetone (DHA).

The cosmetic and/or dermatological compositions according to the invention can also contain pigments or nanopigments (average size of the primary particles: generally ranging from 5 nm to 100 nm, preferably 10 to 50 nm) of coated or uncoated metal oxides such as, for example, nanopigments of titanium dioxide (amorphous or crystallized in rutile and/or anatase form), iron oxide, zinc oxide, zirconium oxide or cerium oxide, which are all photoprotective agents which are well known per se, acting by physically blocking (reflection and/or diffusion) UV radiation. Standard coating agents include alumina and/or aluminum stearate. Such coated or uncoated metal oxide nanopigments are described, in particular, in EP-A-0,518,772 and EP-A-0,518,773.

The compositions in accordance with the present invention can also comprise standard cosmetic additives and adjuvants particularly selected from among fatty substances, organic solvents, ionic or nonionic thickeners, softeners, antioxidants, anti-free-radical agents, opacifiers, stabilizers, emollients, silicones, hydroxy acids, antifoaming agents, moisturizers, vitamins, fragrances, preservatives, surfactants, fillers, sequestering agents, polymers, propellants, basifying or acidifying agents, dyes, colorants or any other constituent usually employed in the cosmetics and/or dermatological fields, in particular for the formulation of antisun/sunscreen compositions in the form of emulsions. Each of the additional ingredients which can be introduced into the compositions of this the invention must be such that it does not substantially disrupt or adversely affect the photostabilization effect exerted by the silane or organosiloxane compounds substituted by a 2-hydroxybenzophenone function on the dibenzoylmethane derivatives.

Exemplary fatty substances include an oil or a wax or mixtures thereof. By the term "oil" is an oily compound which is liquid at room temperature. By the term "wax" is intended a compound which is solid or substantially solid at room temperature, and whose melting point is generally above 35° C.

Exemplary oils include the mineral oils (petroleum jelly); plant oils (sweet almond oil, macadamia oil, grapeseed oil, jojoba oil); synthetic oils such as perhydrosqualene, fatty alcohols, fatty acids or fatty esters (such as $C_{12}$–$C_{15}$ alkyl benzoate marketed under the trademark "Finsolv TN" by Finetex, octyl palmitate, isopropyl lanolate, triglycerides including those of capric/caprylic acid), oxyethylenated or oxypropylenated fatty esters and fatty ethers; silicone oils (cyclomethicone, polydimethylsiloxanes, or PDMS) or fluoro oils; polyalkylenes.

Exemplary waxy compounds include paraffin, carnauba wax, beeswax or hydrogenated castor oil.

And exemplary organic solvents include the lower alcohols and polyols.

The thickeners are advantageously selected from among crosslinked polyacrylic acids and modified or unmodified guar gums and celluloses, such as hydroxypropyl guar gum, methylhydroxyethylcellulose and hydroxypropylmethylcellulose.

The compositions according to the present invention are readily formulated via techniques which are well known to this art, in particular those intended for the preparation of oil-in-water or water-in-oil type emulsions.

The subject compositions, for example, may be in the form of a simple or complex emulsion (O/W, W/O, O/W/O or W/O/W) such as a cream, a milk, a lotion, an ointment or in the form of a gel or a cream gel, a powder or a solid stick and can optionally be packaged as an aerosol and can be in the form of a foam or a spray.

Preferably, the compositions of this invention are in the form of an oil-in-water emulsion.

When formulated as an emulsion, the aqueous phase of this emulsion can comprise a nonionic vesicle dispersion prepared according to known processes (Bangham, Standish and Watkins, *J. Mol. Biol.*, 13, 238 (1965); FR 2,315,991 and FR 2,416,008).

The topically applicable cosmetic and/or dermatological compositions of the invention are well suited for protecting the human epidermis or the hair against ultraviolet radiation, whether as an antisun or sunscreen composition or as a makeup product.

When the cosmetic compositions according to the invention are used to protect the human epidermis against UV rays, or as sunscreen/antisun compositions, they may be formulated as a suspension or a dispersion in solvents or fatty substances, in the form of a nonionic vesicle dispersion or, alternatively, in the form of an emulsion, preferably of oil-in-water type, such as a cream or a milk, or in the form of an ointment, a lotion, a gel, a cream gel, a solid pencil, a stick, an aerosol foam or a spray.

When the cosmetic composition according to the invention are used for protecting the hair, they may be formulated as a shampoo, a lotion, a gel, an emulsion or a nonionic vesicle dispersion and can constitute, for example, a rinse-out composition, to be applied before or after shampooing, before or after dyeing or bleaching, before, during or after permanent-waving or straightening of the hair, a styling or treating lotion or gel, a blow-drying or hairsetting lotion or gel, or a permanent-waving, straightening, dyeing or bleaching composition for the hair.

When the subject compositions are used as makeup products for the eyelashes, the eyebrows or the skin, such as an epidermal treatment cream, a foundation, a tube of lipstick, an eyeshadow, a blusher, a mascara or an eyeliner, they may be in solid or pasty, anhydrous or aqueous form, such as oil-in-water or water-in-oil emulsions, nonionic vesicle dispersions or suspensions.

For example, for the photoprotective/sunscreen formulations in accordance with the invention which comprise a support (vehicle, diluent or carrier) of oil-in-water emulsion type, the aqueous phase (comprising in particular the hydrophilic sunscreening agents) generally constitutes from 50% to 95% by weight, preferably from 70% to 90% by weight, relative to the total weight of the formulation, the oily phase (comprising in particular the lipophilic sunscreening agents) constitutes from 5% to 50% by weight, preferably from 10% to 30% by weight, relative to the total weight of the formulation, and the (co)emulsifier(s) constitute from 0.5% to 20% by weight, preferably from 2% to 10% by weight, relative to the total weight of the formulation.

In order to further illustrate the present invention and the advantages thereof, the following specific examples are given, it being understood that same are intended only as illustrative and in nowise limitative.

EXAMPLE 1

Preparation of the Compound of Formula (8)

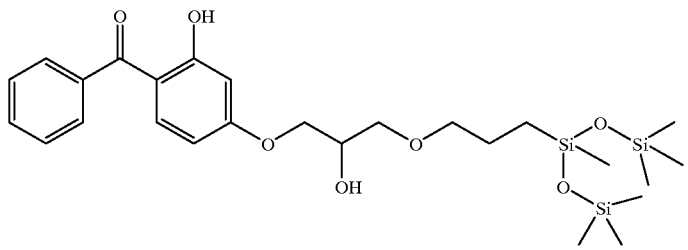

(8)

A mixture of 2,4-dihydroxybenzophenone (10.7 g, 0.05 mol) and 3-glycidyloxypropylbis-(trimethylsiloxy) methylsilane (17.2 g, 0.051 mol) in the presence of tetrabutylammonium iodide (0.2 g) was heated to 110° C. while bubbling nitrogen therethrough for 8 hours. The crude oil obtained was chromatographed on silica (eluent: 60/40 dichloromethane/heptane followed by a gradient down to dichloromethane alone) to provide, as middle fractions, 14.7 g (yield: 53%) of the expected compound of this example in the form of a pale yellow viscous oil:

$UV$(ethanol) $\lambda_{max} = 286$ nm, $\epsilon_{max} = 15{,}090$ $\lambda_{max} = 326$ nm, $\epsilon_{max} = 9890$

EXAMPLE 2

Preparation of the Compound of Formula (11)

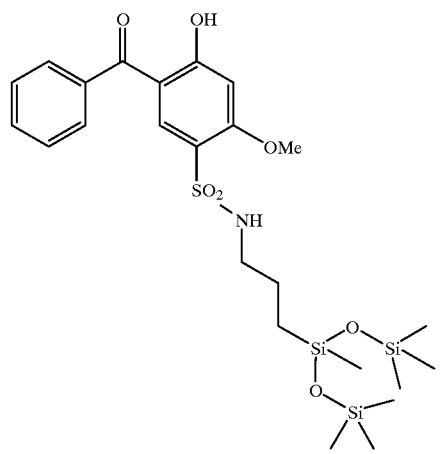

(11)

Thionyl chloride (0.725 ml, 0.01 mol) was added over 5 minutes at room temperature to a suspension of the sodium salt of 5-benzoyl-4-hydroxy-2-methoxybenzenesulfonic acid (3.3 g, 0.01 mol) in 15 ml of dichloromethane. The mixture was heated at 40° C. for 1 hour. This mixture was added portionwise at a temperature of 5–10° C. to a mixture of triethylamine (1 g, 0.01 mol) and 1-amino-3-[1,3,3,3-tetramethyl-1-[(trimethylsilyl)oxy]disiloxanyl]propane (2.8 g, 0.01 mol) in 5 ml of dichloromethane. The mixture was then maintained at room temperature for 2 hours. It was poured onto 50 ml of ice-cold water. The organic phase was recovered, washed with water, dried over sodium sulfate and concentrated. After recrystallization of the solids obtained from a 60/40 ethanol/water mixture, 3.2 g (yield: 56%) of the expected compound of this example were obtained in the form of a pale yellow powder:

m.p.: 190° C. (decomposition) UV (ethanol) $\lambda_{max}$=287 nm, $\epsilon_{max}$=15,210 $\lambda_{max}$=326 nm, $\epsilon_{max}$=9230

EXAMPLE 3

Preparation of the Compound of Formula (4)

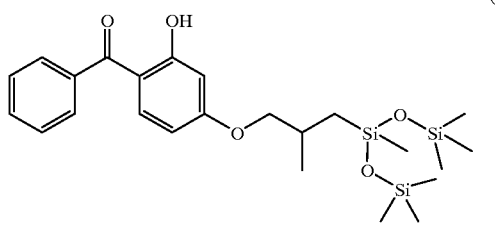

(4)

A mixture of 2,4-hydroxybenzophenone (2.14 g, 0.01 mol), potassium carbonate (2.76 g) and potassium iodide (0.276 g) in 20 ml of DMF was heated to 90° C. while stirring and bubbling nitrogen therethrough. Chloroisobutylheptamethyltrisiloxane (6.26 g, 0.02 mol) was added over 15 minutes at 90° C. The mixture was heated at 90–100° C. for 16 hours. The reaction mixture was poured into ice and extracted with dichloromethane. The organic phase was recovered, washed with water, dried over sodium sulfate and concentrated. The crude oil obtained was chromatographed on silica (eluent: 50/50 dichloromethane/heptane) to give 2.1 g (yield: 43%) of the expected compound of this example in the form of a pale yellow oil: UV (ethanol) $\lambda_{max}$=286 nm, $\epsilon_{max}$=15, 550 $\lambda_{max}$=326 nm, $\epsilon_{max}$=9920

EXAMPLE 4

Compositions A and B described below in Table (I) were formulated (the amounts are expressed as percentages by weight relative to the total weight of the composition):

TABLE (I)

| Ingredients | Composition A (comparative) | Composition B (invention) |
| --- | --- | --- |
| Isopropyl myristate | 30 | 30 |
| Parsol 1789 | 1.5 | 1.5 |
| Compound of formula (5) | — | 5 |
| Ethanol | qs 100 | qs 100 |

Composition B (invention) indicated above also comprised 5% by weight of a silicone compound (5) containing a 2-hydroxybenzophenone function according to the invention, corresponding to the above formula (I) and having the structure:

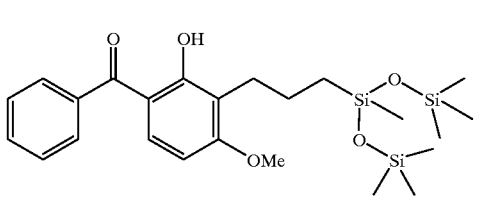

(5)

This compound is described in FR-A-2,657,351 and synthesized according to the procedure of Example 1 of this '351 patent.

For each of these compositions, the percentage of residual Parsol 1789 (4-tert-butyl-4'-methoxydibenzoylmethane) after UV irradiation was determined according to the following protocol:

3 test samples and 3 control samples were prepared for each formula. 2 μl/cm² of formula were deposited by micropipette onto frosted Quartz plates. The test plates were exposed for 2 h 50 min in a Heraeus Suntest fitted with a 1 kW Xenon lamp (which corresponds to an equivalent of 1.7 UVA hours and 3 UVB hours) and the control plates were stored for the same time and at the same temperature (35–40° C.) in darkness.

After this time, the screening agents were extracted by immersing each plate in 50 g of absolute ethanol and treating them with ultrasound for 15 min to ensure good extraction. The solutions obtained were analyzed by high performance liquid chromatography. For each formula tested, the residual content of Parsol 1789 after exposure was provided by the ratio of its concentration in the exposed sample to its concentration in the unexposed sample.

The results obtained are reported in Table II below:

TABLE (II)

| COMPOSITION | RESIDUAL PARSOL 1789 |
| --- | --- |
| A (comparative) | 2% |
| B (invention) | 36% |

These results evidence that the presence of the silicone compound (5) improved the photostability of Parsol 1789 after exposure to UV.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photostable, topically applicable cosmetic/deratological sunscreen composition suited for the UV-photoprotection of human skin and/or hair, comprising (1) a UV-photoprotecting effective amount of at least one dibenzoylmethane sunscreen compound and (2) a photostabilizing effective amount of at least one silane or organosiloxane bearing a 2-hydroxybenzophenone substituent.

2. The cosmetic/dermatological sunscreen composition as defined by claim 1, comprising (2) a photostabilizing effective amount of at least one silane bearing a 2-hydroxybenzophenone substituent.

3. The cosmetic/dermatological sunscreen composition as defined by claim 1, comprising (2) a photostabilizing effective amount of at least one organosiloxane bearing a 2-hydroxybenzophenone substituent.

4. The cosmetic/dermatological sunscreen composition as defined by claim 1, formulated into a topically applicable, cosmetically/dermatologically acceptable vehicle, diluent or carrier therefor.

5. The cosmetic/dermatological sunscreen composition as defined by claim 1, said at least one silane or organosiloxane bearing a 2-hydroxybenzophenone substituent having the structural formula (I):

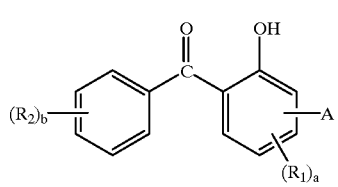

(I)

in which $R_1$ and $R_2$, which may be identical or different, are each a hydrogen atom, an OH radical, a saturated or unsaturated, linear or branched $C_1$–$C_{10}$ alkyl radical or a linear or branched $C_1$–$C_{10}$ alkoxy radical; a is an integer ranging from 1 to 3; b is an integer ranging from 1 to 5; A is a radical of formula —L—W wherein L is a divalent radical of formula (IIa) or (IIb) below:

$$—CH_2—CHR_3—[C(R_4)_2]_{\overline{m}}—(CO)_{\overline{n}}—(O)_{\overline{o}}—(Z)_{\overline{p}}—(Y)_{\overline{q}}—$$ (IIa)

$$—CH{=}CR_3—[C(R_4)_2]_{\overline{m}}—(CO)_{\overline{n}}—(O)_{\overline{o}}—(Z)_{\overline{p}}—(Y)_{\overline{q}}—$$ (IIb)

in which $R_3$ and $R_4$, which may be identical or different, are each a hydrogen atom or a linear or branched $C_1$–$C_5$ alkyl radical; Z is a linear or branched, saturated or unsaturated $C_1$–$C_6$ diyl radical optionally substituted with a hydroxyl or linear or branched, saturated or unsaturated $C_2$–$C_8$ alkyl radical; Y represents —O—, —$NR_5$—, —$SO_2NH$—, —(CO)O—, —(CO)NH— or —O(CO)NH—, wherein $R_5$ is a hydrogen atom or a $C_1$–$C_5$ alkyl radical; m is an integer ranging from 0 to 10; n is 0 or 1; o is 0 or 1; p is 0 or 1; q is 0 or 1; W is a radical of one of the formulae (1), (2) or (3) below:

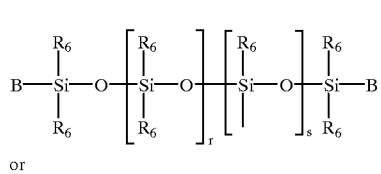

or

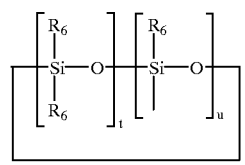

or

—Si($R_7$)$_3$ (3)

in which the radicals $R_6$, which may be identical or different, are each a linear or branched $C_1$–$C_{30}$ alkyl, phenyl, 3,3,3-trifluoropropyl or trimethylsilyloxy radical, at least 80%, by number, of the radicals $R_6$ being methyl radicals; the radicals $R_7$, which may also be identical or different, are each a linear or branched $C_1$–$C_{30}$ alkyl or phenyl radical; the radicals B, which may be identical or different, are each a radical $R_6$ or a radical X having the following formula:

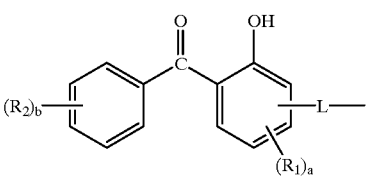

in which $R_1$, $R_2$, L, a and b are as defined above; r is an integer ranging from 0 to 200, inclusive; s is an integer ranging from 0 to 50, inclusive, with the proviso that, if s=0, at least one of the two radicals B is X; u is an integer ranging from 1 to 10, inclusive and t is an integer ranging from 0 to 10, inclusive, with the proviso that t+u is greater than or equal to 3.

6. The cosmetic/dermatological sunscreen composition as defined by claim 5, wherein formula (I), at least one of the following conditions is satisfied:

$R_1 = R_2 = R_3 = R_5 = H$,
$n = 0$,
$q = 1$.

7. The cosmetic/dermatological sunscreen composition as defined by claim 5, wherein formula (I), at least one of the following conditions is satisfied:

$R_6$ is methyl;

B is methyl;

r ranges from 5 to 20, inclusive;

s ranges from 2 to 15, inclusive;

t+u ranges from 3 to 10, inclusive;

m=1;

$R_3$ is a hydrogen atom or a methyl radical.

8. The cosmetic/dermatological sunscreen composition as defined by claim 5, wherein formula (I), s=0.

9. The cosmetic/dermatological sunscreen composition as defined by claim 5, said compound having the structural formula (I) being selected from among those having the following formulae:

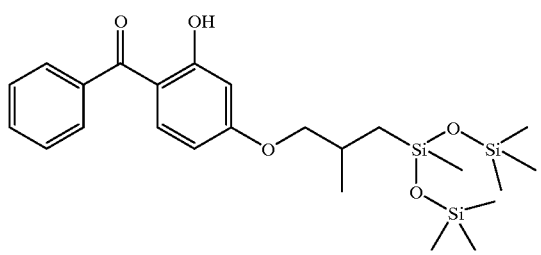
(4)
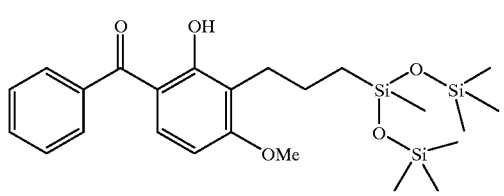
(5)
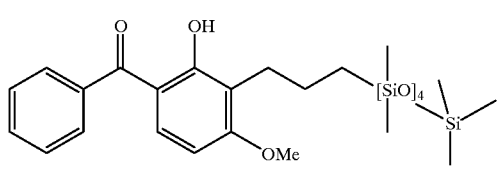
(6)
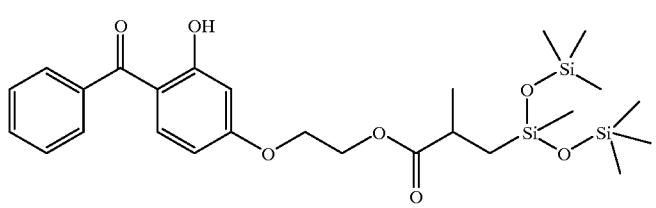
(7)
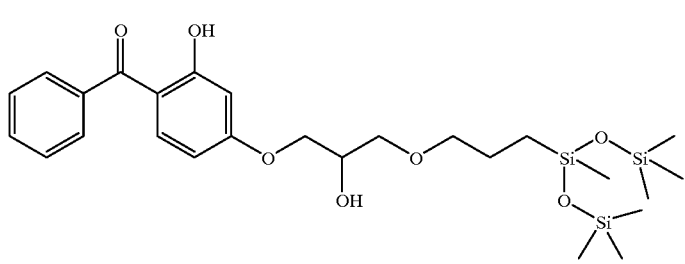
(8)
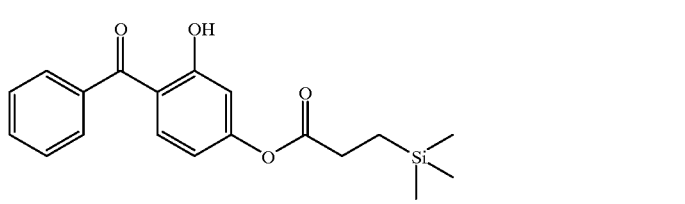
(9)
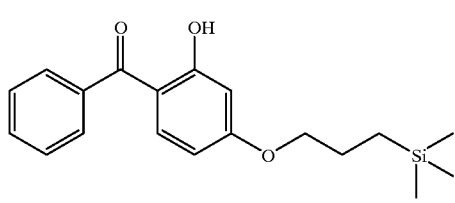
(10)

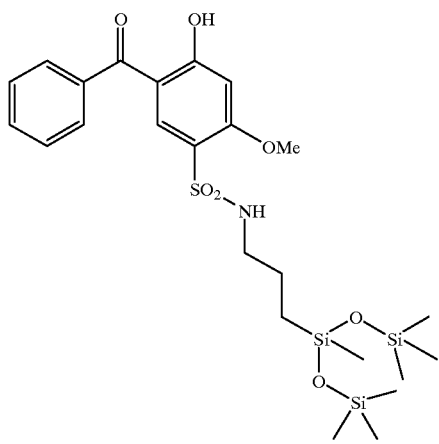

(11)

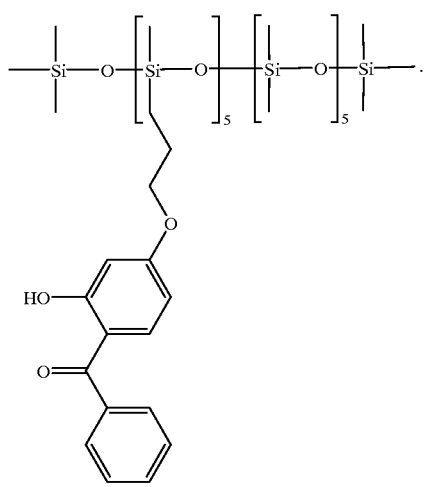

(12)

10. The cosmetic/dermatological sunscreen composition as defined by claim 5, wherein formula (I), p is equal to 1 and the radical Z is a linear or branched, saturated or unsaturated $C_1$–$C_6$ diyl radical containing a hydroxyl or linear or branched, saturated or unsaturated $C_2$–$C_8$ alkyl radical.

11. The cosmetic/dermatological sunscreen composition as defined by claim 9, said compound of formula (I) having the structural formula:

12. The cosmetic/dermatological sunscreen composition as defined by claim 5, wherein formula (I), W is a radical of formula (3) and n=0.

13. The cosmetic/dermatological sunscreen composition as defined by claim 9, said compound of formula (I) having the structural formula:

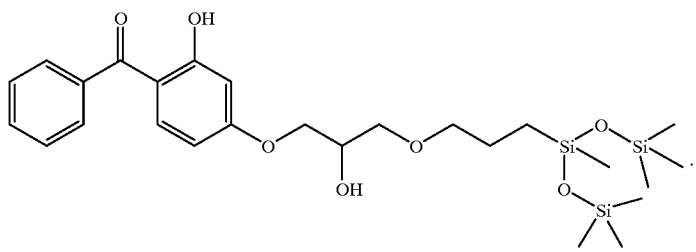

(8)

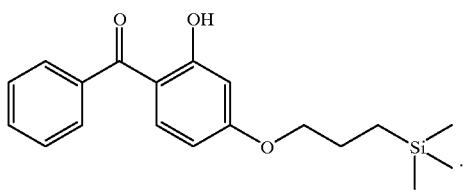

(10)

14. The cosmetic/dermatological sunscreen composition as defined by claim 1, said at least one dibenzoylmethane sunscreen compound comprising 2-Methyldibenzoylmethane;
4-Methyldibenzoylmethane;
4-Isopropyldibenzoylmethane;
4-Tert-butyldibenzoylmethane;
2,4-Dimethyldibenzoylmethane;
2,5-Dimethyldibenzoylmethane;
4,4'-Diisopropyldibenzoylmethane;
4,4'-Dimethoxydibenzoylmethane;
4-Tert-butyl-4'-methoxydibenzoylmethane;
2-Methyl-5-isopropyl-4'-methoxydibenzoylmethane;
2-Methyl-5-tert-butyl-4'-methoxydibenzoylmethane;
2,4-Dimethyl-4'-methoxydibenzoylmethane; or
2,6-Dimethyl-4-tert-butyl-4'-methoxydibenzoylmethane.

15. The cosmetic/dermatological sunscreen composition as defined by claim 14, said at least one dibenzoylmethane sunscreen compound comprising 4-(tert-butyl)-4'-methoxydibenzoylmethane.

16. The cosmetic/dermatological sunscreen composition as defined by claim 14, said at least one dibenzoylmethane sunscreen compound comprising 4-isopropyldibenzoylmethane.

17. The cosmetic/dermatological sunscreen composition as defined by claim 1, said at least one dibenzoylmethane sunscreen compound comprising from 0.01% to 10% by weight thereof.

18. The cosmetic/dermatological sunscreen composition as defined by claim 17, said at least one dibenzoylmethane sunscreen compound comprising from 0.1% to 6% by weight thereof.

19. The cosmetic/dermatological sunscreen composition as defined by claim 1, said at least one silane or organosiloxane comprising at least 0.5% by weight thereof.

20. The cosmetic/dermatological sunscreen composition as defined by claim 19, said at least one silane or organosiloxane comprising from 0.5% to 20% by weight thereof.

21. The cosmetic/dermatological sunscreen composition as defined by claim 1, comprising an oil-in-water emulsion.

22. The cosmetic/dermatological sunscreen composition as defined by claim 1, comprising a water-in-oil emulsion.

23. The cosmetic/dermatological sunscreen composition as defined by claim 1, further comprising at least one additional hydrophilic or lipophilic UVA- and/or UVB- sunscreen.

24. The cosmetic/dermatological sunscreen composition as defined by claim 23, further comprising at least one cinnamic sunscreen, salicylic sunscreen, benzylidene camphor sunscreen, benzotriazole sunscreen, benzimidazole sunscreen, triazine sunscreen, benzomalonate sunscreen, β,β'-diphenylacrylate sunscreen, p-aminobenzoic acid sunscreen, sunscreen polymer and/or sunscreen silicone.

25. The cosmetic/dermatological sunscreen composition as defined by claim 1, further comprising at least one active agent for the artificial tanning and/or bronzing of human skin.

26. The cosmetic/dermatological sunscreen composition as defined by claim 1, further comprising at least one cosmetically/dermatologically acceptable adjuvant or additive.

27. The cosmetic/dermatological sunscreen composition as defined by claim 26, said at least one adjuvant or additive comprising a fat, organic solvent, ionic or nonionic thickening agent, softener, antioxidant, anti-free-radical antioxidant, opacifying agent, stabilizing agent, emollient, silicone, hydroxy acid, antifoaming agent, vitamin, fragrance, preservative, surfactant, filler, sequestering agent, moisturizer, polymer, propellant, basifying or acidifying agent, dye, colorant, or mixture thereof.

28. The cosmetic/dermatological sunscreen composition as defined by claim 1, further comprising a photoprotecting effective amount of particulates of at least one inorganic pigment or nanopigment.

29. The cosmetic/dermatological sunscreen composition as defined by claim 28, said at least one pigment or nanopigment comprising titanium dioxide, zinc oxide, iron oxide, zirconium oxide, cerium oxide, or mixture thereof.

30. The cosmetic/dermatological sunscreen composition as defined by claim 1, comprising a nonionic vesicle dispersion, lotion, cream, milk, gel, cream gel, ointment, suspension, dispersion, powder, solid stick, foam or spray.

31. The cosmetic/dermatological sunscreen composition as defined by claim 1, comprising a makeup.

32. The cosmetic/dermatological sunscreen composition as defined by claim 1, comprising a stick, pencil, solid or paste.

33. The cosmetic/dermatological sunscreen composition as defined by claim 1, comprising a shampoo, rinse, styling lotion or gel, blow-drying or hairsetting lotion or gel, or permanent-waving, straightening, dyeing or bleaching composition for the hair.

34. The cosmetic/dermatological sunscreen composition as defined by claim 1, comprising a foundation, lipstick, mascara, eyeshadow, eyeliner, or blusher.

35. A regime/regimen for photoprotecting human skin and/or hair against the deleterious effects of ultraviolet radiation, comprising topically applying thereto an effective amount of the cosmetic/dermatological sunscreen composition as defined by claim 1.

36. A regime/regimen for photoprotecting human skin and/or hair against the deleterious effects of solar radiation, comprising topically applying thereto an effective amount of the cosmetic/dermatological sunscreen composition as defined by claim 1.

37. A compound having the structural formula (I'):

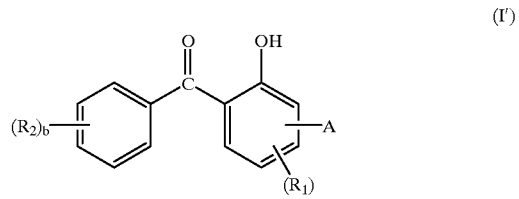

(I')

in which $R_1$ is a hydrogen atom, an OH radical, a saturated or unsaturated, linear or branched $C_1$–$C_{10}$ alkyl radical or a linear or branched $C_1$–$C_{10}$ alkyl radical; $R_2$ is a hydrogen atom, a saturated or unsaturated, linear or branched $C_1$–$C_{10}$ alkyl radical or a linear or branched $C_1$–$C_{10}$ alkoxy radical; a is an integer ranging from 1 to 3; b is an integer ranging from 1 to 5; A is a radical of formula —L—W wherein L is a divalent radical of the following formulae:

(IIa)

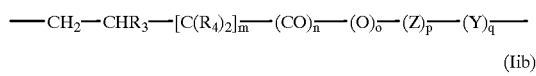

(IIb)

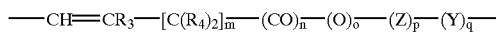

in which $R_3$ and $R_4$, which may be identical or different, are each a hydrogen atom or a linear or branched $C_1$–$C_5$ alkyl radical; Z is a linear or branched, saturated or unsaturated $C_1$–$C_6$ diyl radical substituted by a hydroxyl or linear or branched, saturated or unsaturated $C_2$–$C_8$ alkyl radical; Y is —O—, —NR$_5$—, —SO$_2$NH—, —(CO)O—, —(CO)NH— or —O(CO)NH—, wherein $R_5$ is a hydrogen atom or a $C_1$–$C_5$ alkyl radical; m is an integer ranging from 0 to 10; n is 0 or 1; o is 0 or 1; p is 0 or 1; q is 0 or 1; W is a radical of formulae (1), (2) or (3) below:

(1)

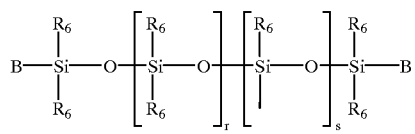

(2)

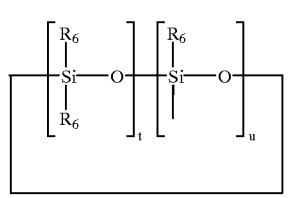    or (3)

—Si(R$_7$)$_3$ in which the radicals $R_6$, which may be identical or different, are each a linear or branched $C_1$–$C_{30}$ alkyl, phenyl, 3,3,3-trifluoropropyl or trimethylsilyloxy radical, at least 80%, by number, of said radicals $R_6$ being methyl radicals; the radicals $R_7$, which may be identical or different, are each a linear or branched $C_1$–$C_{30}$ alkyl or phenyl radical; the radicals B, which may be identical or different, are each a radical $R_6$ and the radical X has the following structural formula:

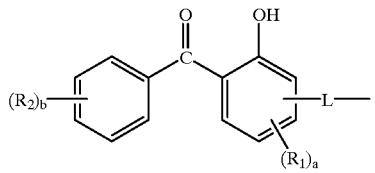

in which $R_1$, $R_2$, L, a and b are as defined above; r is an integer ranging from 0 to 200, inclusive; s is an integer ranging from 0 to 50, inclusive, with the proviso that, if s=0, at least one of the two symbols B is x; and u is an integer ranging from 1 to 10, inclusive and t is an integer ranging from 0 to 10, inclusive, with the proviso that t+u is greater than or equal to 3.

38. A compound as defined by claim 37, having the structural formula:

(8)

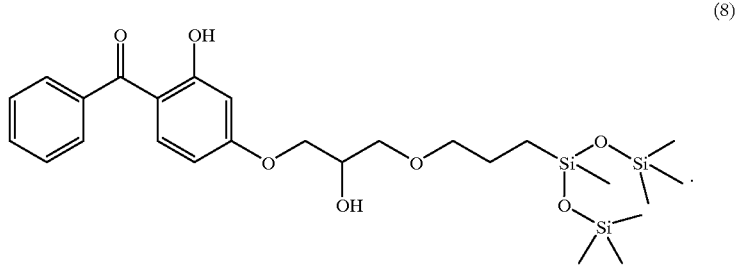

39. A compound as defined by claim 37, having the structural formula (I″):

(I″)

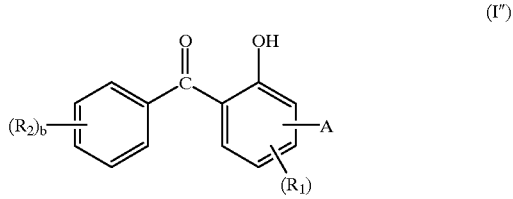

in which $R_1$ is a hydrogen atom, an OH radical, a saturated or unsaturated, linear or branched $C_1$–$C_{10}$ alkyl radical or a linear or branched $C_1$–$C_{10}$ alkyl radical; $R_2$ is a hydrogen atom, a saturated or unsaturated, linear or branched $C_1$–$C_{10}$ alkyl radical or a linear or branched $C_1$–$C_{10}$ alkoxy radical; a is an integer ranging from 1 to 3; b is an integer ranging from 1 to 5; A is a radical of formula —L—W wherein L is a divalent radical of the formulae (IIa) or (IIb) below:

(IIa)

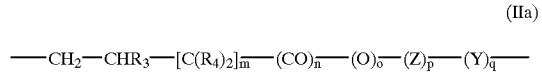

-continued

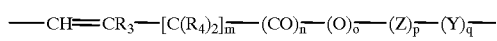
(IIb)

in which the radicals $R_3$ and $R_4$, which may be identical or different, are each a hydrogen atom or a linear or branched $C_1$–$C_5$ alkyl radical; Z is a linear or branched, saturated or unsaturated $C_1$–$C_6$ diyl radical substituted by a hydroxyl or linear or branched, saturated or unsaturated $C_2$–$C_8$ alkyl radical; Y is —O—, —$NR_5$—, —$SO_2NH$—, —(CO)O—, —(CO)NH— or —O(CO)NH—, wherein $R_5$ is a hydrogen atom or a $C_1$–$C_5$ alkyl radical; m is an integer ranging from 0 to 10; n is 0 or 1; o is 0 or 1; p is 0 or 1; q is 0 or 1; W is a radical of formula (3) below:

 (3)

in which the radicals $R_7$, which may be identical or different, are each a linear or branched $C_1$–$C_{30}$ alkyl or phenyl radical.

40. A compound as defined by claim 37, having the structural formula:

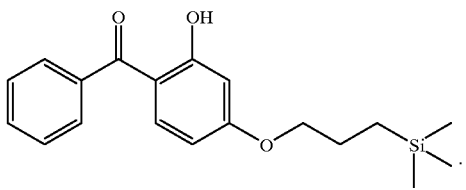
(10)

41. A compound as defined by claim 37, wherein formula (I), W is a radical (1).

42. A compound as defined by claim 37, wherein formula (I), W is a radical (2).

43. A compound as defined by claim 37, wherein formula (I), W is a radical (3).

* * * * *